United States Patent
Dunbar

(10) Patent No.: US 9,949,685 B2
(45) Date of Patent: Apr. 24, 2018

(54) INSTRUMENTED SLEEVE

(71) Applicant: Howmedica Osteonics Corp., Mahwah, NJ (US)

(72) Inventor: Michael James Dunbar, Duncans Cove (CA)

(73) Assignee: Howmedica Osteonics Corp., Mahwah, NJ (US)

( * ) Notice: Subject to any disclaimer, the term of this patent is extended or adjusted under 35 U.S.C. 154(b) by 40 days.

(21) Appl. No.: 14/163,403

(22) Filed: Jan. 24, 2014

(65) Prior Publication Data

US 2014/0213929 A1     Jul. 31, 2014

Related U.S. Application Data

(60) Provisional application No. 61/756,655, filed on Jan. 25, 2013.

(51) Int. Cl.
*A61B 5/00*    (2006.01)
*A61B 5/11*    (2006.01)

(52) U.S. Cl.
CPC .......... *A61B 5/4827* (2013.01); *A61B 5/6812* (2013.01); *A61B 5/743* (2013.01); *A61B 5/744* (2013.01); *A61B 5/1114* (2013.01); *A61B 5/6828* (2013.01); *A61B 2562/0247* (2013.01)

(58) Field of Classification Search
CPC ............................ A61B 5/4824; A61B 5/4827
USPC ....................................................... 600/557
See application file for complete search history.

(56) References Cited

U.S. PATENT DOCUMENTS

| | | | |
|---|---|---|---|
| 5,751,973 A | 5/1998 | Hassett | |
| 6,216,545 B1 | 4/2001 | Taylor | |
| 6,543,299 B2 | 4/2003 | Taylor | |
| 7,201,063 B2 | 4/2007 | Taylor | |
| 8,161,826 B1 | 4/2012 | Taylor | |
| 8,533,879 B1 | 9/2013 | Taylor | |
| 2002/0076681 A1* | 6/2002 | Leight | G09B 23/28 434/273 |
| 2004/0019303 A1* | 1/2004 | Thomson | A61B 5/103 600/595 |
| 2009/0264737 A1* | 10/2009 | Haechler | A61B 19/52 600/424 |
| 2012/0127157 A1* | 5/2012 | Adler | G06Q 50/24 345/419 |
| 2012/0234105 A1 | 9/2012 | Taylor | |
| 2012/0259649 A1* | 10/2012 | Mallon | G06Q 10/06 705/2 |

(Continued)

OTHER PUBLICATIONS

Pantelopoulos, Alexandros, and Nikolaos Bourbakis. "A survey on wearable sensor-based systems for health monitoring and prognosis." Systems, Man, and Cybernetics, Part C: Applications and Reviews, IEEE Transactions on 40.1 (2010): 1-12.*

(Continued)

*Primary Examiner* — Michael C Stout
*Assistant Examiner* — Nicholas E Kolderman
(74) *Attorney, Agent, or Firm* — Lerner, David, Littenberg, Krumholz & Mentlik, LLP

(57) ABSTRACT

A sleeve is provided for determining the location and severity of joint pain in a patient. The sleeve includes sensors in communication with a display device that allow for areas of pain to be quickly and accurately determined. Methods of utilizing the sleeve are also disclosed.

15 Claims, 3 Drawing Sheets

(56) References Cited

U.S. PATENT DOCUMENTS

2013/0085410 A1* 4/2013 Alberth ................ A61B 5/7435
600/557

OTHER PUBLICATIONS

Thompson, Laura R., et al. "The knee pain map: reliability of a method to identify knee pain location and pattern." Arthritis Care & Research 61.6 (2009): 725-731.*

David A.J. Wilson, Cheryl L. Hubley-Kozey, et. al. Pre-operative muscle activation patterns during walking are associated with TKA tibial implant migration. Clinical biomechanics (Bristol, Avon) Nov. 1, 2012 (vol. 27 issue 9 pp. 936-942 DOI: 10.1016/j.clinbiomech.2012.06.012).

Huisman, G.; Darriba Frederiks, A.; van Dijk, B.; Hevlen, D.; Krose, B. "The TaSSt: Tactile sleeve for social touch," World Haptics Conference (WHC), 2013, vol., No., pp. 211,216, Apr. 14-17, 2013.

Owano, Nancy. MYO Armband to Muscle into Computer Control (w/video). Apr. 28, 2013. Web The Hong Kong Polytechnic University <http://www.polyu.edu.hk>, Science Daily, http://www.sciencedaily.com/releases/2012/11/121108140845.htm, Nov. 2011.

* cited by examiner

INSTRUMENTED SLEEVE

CROSS-REFERENCE TO RELATED APPLICATIONS

The present application claims the benefit of the filing date of U.S. provisional patent application No. 61/756,655 filed Jan. 25, 2013, the disclosure of which is hereby incorporated herein by reference.

The present invention relates to devices for determining the location, quality and severity of pain in joints, such as the knee. In particular, the present invention relates to a sleeve configured to be worn over a joint that communicates with a computer or the like to accurately and precisely determine the location and severity of such joint pain. In addition, the present invention has applicability to determining the proper operation of a joint, such as the knee. Essentially, sleeves in accordance with the present invention may be worn over a joint to allow for information pertaining to the kinematics of the particular joint to be viewable on a display.

One common problem faced by surgeons is accurately and precisely determining the location and severity of pain in joints, such as the knee joint, of their patients. Currently, surgeons or other medical professionals make use of two-dimensional pain drawings of the joint, and subjective health outcome questionnaires, including questions specific to pain and function in order to work with the patient in identifying the joint problems. These tools are very subjective in nature, and lead to imprecise and inaccurate determinations of both the location and severity of the joint pain. While devices such as the knee KG™ offered by Emovi can be utilized to determine a kinematic analysis of the knee, devices such as this do not aid in determining the location and/or severity of any pain.

Therefore, there exists a need for a device and method that can aid a surgeon in accurately and precisely determining the location and severity of joint pain in a patient.

SUMMARY OF THE INVENTION

A first aspect of the present invention is a sleeve including a fabric interwoven with sensors. The sensors are in communication with a display that displays pain information in a joint.

A second aspect of the present invention is a kit including a fabric interwoven with sensors and a computing device in communication with the sensors. The sensors aid in identifying pain in a joint and the computing device analyzes information provided by the sensors. A display may also be provided for displaying pain information.

A third aspect of the present invention is a method including the steps of placing a sleeve over a portion of a body, the sleeve including fabric interwoven with sensors, touching portions of the sleeve corresponding to pain areas in the portion of the body and displaying information pertaining to the pain areas on a display.

A further aspect of the present invention is a sleeve that includes EMG sensors to sense muscle firing and the like. Such sleeve may be utilized with a computing device and display in order to convey EMG information to the user.

DESCRIPTION OF THE DRAWINGS

A more complete appreciation of the subject matter of the present invention(s) and of the various advantages thereof can be realized by reference to the following detailed description in which reference is made to the accompanying drawings in which.

DETAILED DESCRIPTION OF DRAWINGS

Figure 1:
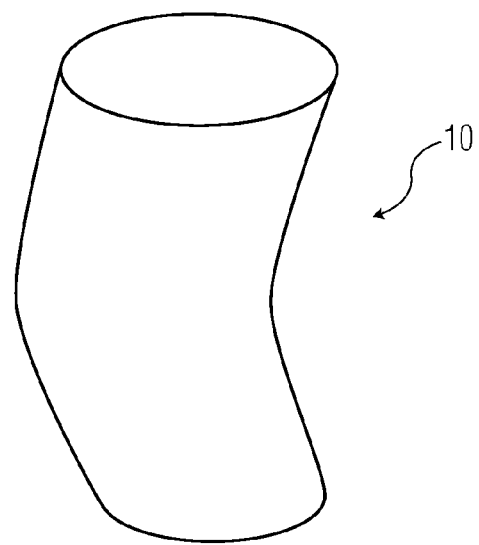
FIG. 1 is a perspective view of a sleeve according to an embodiment of the present invention.

With reference to FIG. 1, the present invention includes a sleeve constructed of a "smart" fabric that is worn over the joint of a patient. In particular, as shown in FIG. 1, a sleeve 10 is designed to fit over a human knee. Of course, although sleeve 10 is specifically shown as being associated with a knee joint, it is within the scope of the present invention to design sleeves associated with other joints of the human body. For instance, a sleeve in accordance with the present invention may be utilized in conjunction with the elbow (similar to sleeve 10, but sized for the elbow) or ankle joints (potentially shaped like a sock, ankle brace or the like). Moreover, various sizes and/or shapes of the sleeve can be provided in accordance with the present invention. For instance, it is well within the scope of the invention to provide sleeves 10 that are sized for differently sized patients.

The "smart" fabric that sleeve 10 is constructed of preferably includes a fabric interwoven with sensors that are sensitive to touch. These sensors can communicate with a computer, tablet, or the like via any known mode of communication, for instance, via wires or wirelessly. Moreover, these sensors (not specifically shown in the figures) can be sensitive with the simple touch of a finger, or through the use of a secondary device, such as a stylus. Sensors for use in the present invention are known and, any suitable fabric can be used in the sleeve. For instance, an article entitled "The TaSST: Tactile Sleeve for Social Touch" by Huisman et al., the disclosure of which is hereby incorporated by reference herein, describes a touch-sensitive sleeve that allows two people to communicate over a distance. A similar constructed sleeve may be utilized in accordance with the present invention. Preferably, the sleeve is constructed of a material flexible enough for attachment to the body while maintaining comfort for the patient. Although sleeve 10 is discussed as including sensors 12 interwoven into a fabric, it is contemplated that other means of attaching sensors to the fabric of the sleeve may be employed. For instance, sensors 12 may be affixed in any manner to an outer or inner portion of sleeve 10. Likewise, it contemplated to utilize existing and future fabric that can conduct electricity in sleeve 10. For instance, fabrics are known that are pressure sensitive and constructed of flexible polymers and non-carbon materials. The conductive nano-carbon materials are laced onto the polymer to create a thin layer that can transfer electricity. When stretched or pressed, the thickness of the layer changes, which leads to a change in the electric current and resistance. Thus, the fabric will react to a pull or compression with an increase in resistance so that strain and pressure can be measured. These fabrics provide a suitable material for use in the present invention, without the need for separate sensors to be otherwise attached to the fabric.

Figure 2:
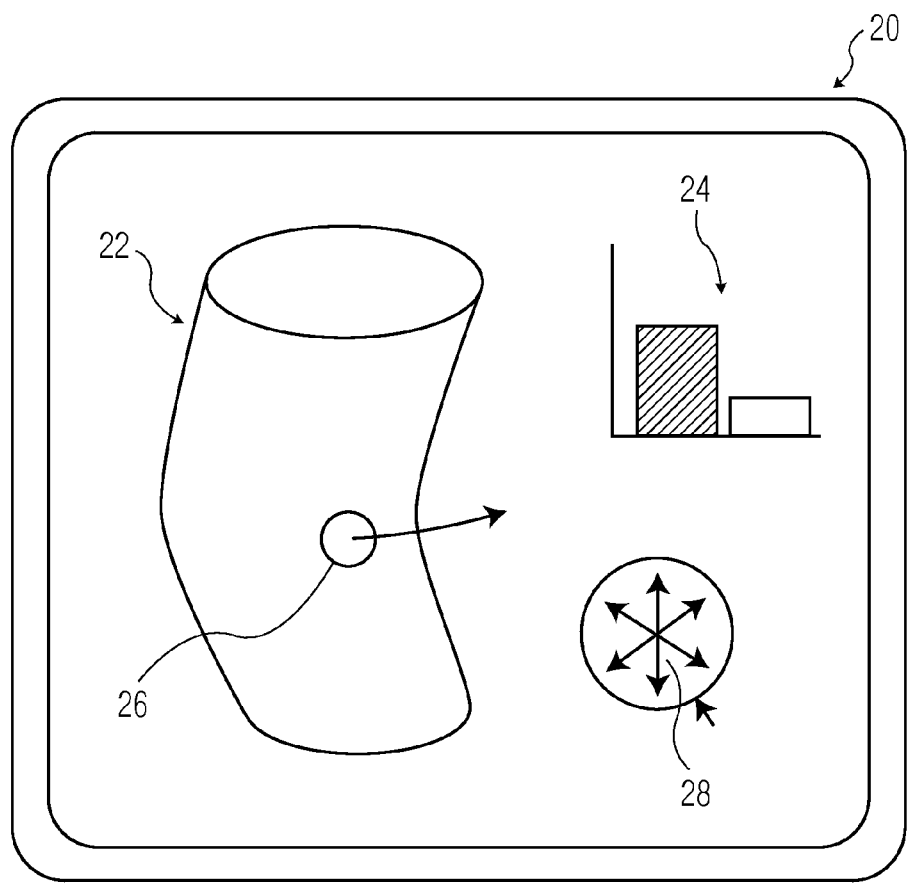
FIG. 2 is a view of a display according to an embodiment of the present invention.
Figure 3:
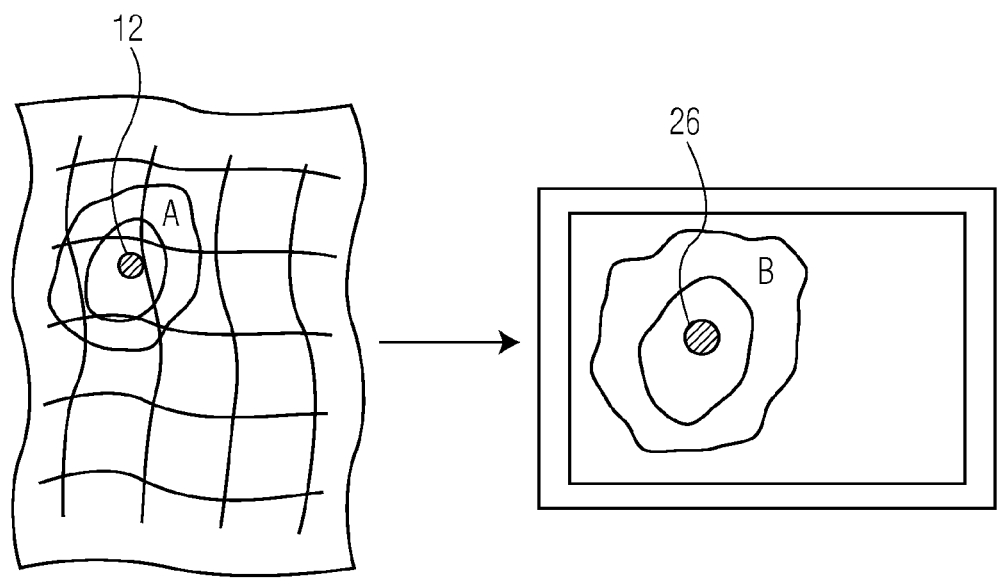
FIG. 3 is an illustration of the relationship between an area of the sleeve shown in FIG. 1 and a portion of the display shown in FIG. 2.

A display 20 is depicted in FIG. 2. Preferably, display 20 is part of or attached to a processing device, such as a computer or tablet, which is in turn in communication with sensors 12 of sleeve 10. Display 20 includes a three-dimensional avatar 22 of the joint (in this case, a knee) which includes an area 26 corresponding to a given sensor 12 in sleeve 10 (this relationship is further depicted in FIG. 3). As shown, a graphical user interface 24 depicts values measured by sensor 12 upon the touch by the patient or practitioner, such as the pressure and/or area of the touch. Preferably, sensor 12 is designed so that the touch correlates to the pain being experienced by the patient. Of course, other values could be represented on display 20, in many different manners. Display 20 may also include a controller 28 for manipulating avatar 22. For instance, in the embodiment shown, avatar 22 can be rotated (to show other areas of the joint) and/or zoomed.

In use, sleeve 10 is placed over a patient's joint and the particular patient's anatomy is calibrated to the sleeve by registering cardinal points by touching the sleeve during the registration process. For instance, in the case of the knee, the cardinal points may include the patella, medial and/or lateral epicondyle, tibial tubrical, and/or joint line, among others. Once registered, the sleeve can then display in real time a three-dimensional specific avatar 22 of the knee on display 20. During a pain analysis with the surgeon, the patient may be asked to touch where on their knee they experience symptoms, such as pain. The touch applied to sleeve would be represented by area 26 on avatar 22 and the corresponding pressure per area information may be displayed via interface 24. This data may be recorded and/or logged.

In addition to aiding a surgeon or other medical professional in understanding the patient's particular pain issues, the sleeve of the present invention has other purposes. For instance, sleeve 10 could be used to collect data on multiple pathologies of joint, including the spectrum of osteoarthritis from mild symptoms to joint replacements. The pressure data captured, as described above, could be investigated with statistical analysis to look for patterns. These patterns would subsequently be correlated to simultaneously collected data such as radiographic, kinematic, and subject health outcome metrics. In addition, sleeve 10 of the present invention could be utilized to validate joint pain specific questionnaires such as those currently used. Still further, the use of sleeve 10 can suggest to a surgeon diagnoses with the probability assessment of accuracy. In this regard, data collected against a wide range of pathologies, patterns of pain and symptom descriptions, may help with suggesting the diagnoses.

Moreover, sleeve 10 could be utilized to look at pressure/contact patterns through range of motion, or dynamic exercises, such as stair climbing. The resulting contact pressure pattern may have correlations to certain pathologies. For instance, sagittal instability post total knee replacement may present with a different contact pressure pattern while descending stairs then midflection instability might. Likewise, a surgeon or other medical professional could apply pressure via their hands or other devices in a prescribed pattern to determine the stability of the joint. Pressure readings provided by sleeve 10, as well as patient feedback with regard to pain, can be monitored to determine weakened areas of the joint. This can be done through a range of motions, for instance, with respect to the knee joint, during flexion, extension and pivoting of the femur with respect to the tibia.

Figure 4:
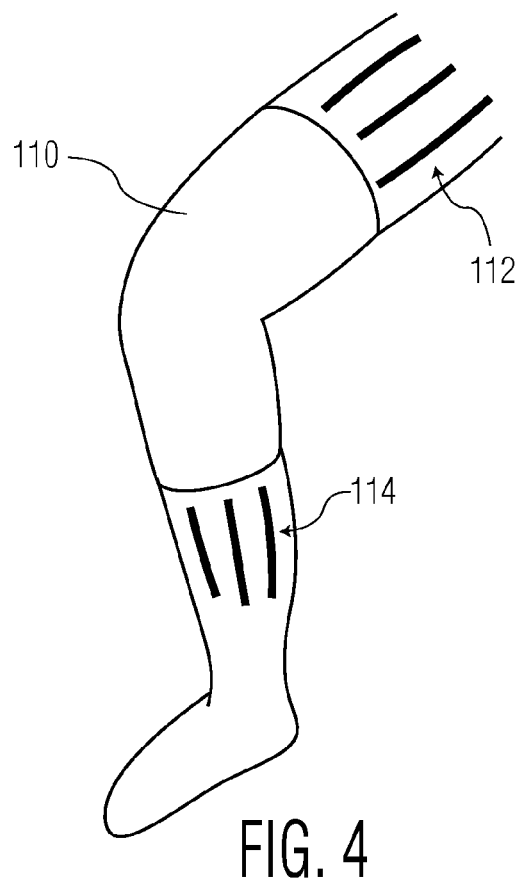
FIG. 4 is a perspective view of a sleeve according to another embodiment of the present invention.

As is outlined in an article entitled, "Pre-operative muscle activation patterns during walking are associated with TKA tibial implant migration" by Dunbar et al., the disclosure of which is hereby incorporated by reference herein, electro-myographical ("EMG") information from the musculature surrounding a joint may be beneficial in determining issues in the operation of the joint. A sleeve according to another embodiment includes EMG sensors, which can sense and transmit EMG information. For instance, as shown in FIG. 4, a sleeve 110 is provided which includes EMG sensors throughout its construction. These sensors can provide information pertaining to firing and operation of muscles 112 and 114, as well as nerve operation. An example of the technology that can be employed in sleeve 110 is included in the MYO armband offered by Thalmic Labs of Waterloo, Ontario, although that device is mainly utilized to control electronic devices such as computers or the like. Local sensing of adverse muscle firing patterns can be indentified utilizing sleeve 110 and communicated to a surgeon or other medical professional via a display or the like as described above. Tactile feedback can then be provided in the location of the misfiring muscle group via built in sensors in sleeve 110. The use of sleeve 110 may be particularly useful in a rehabilitation scenario.

Figure 5:
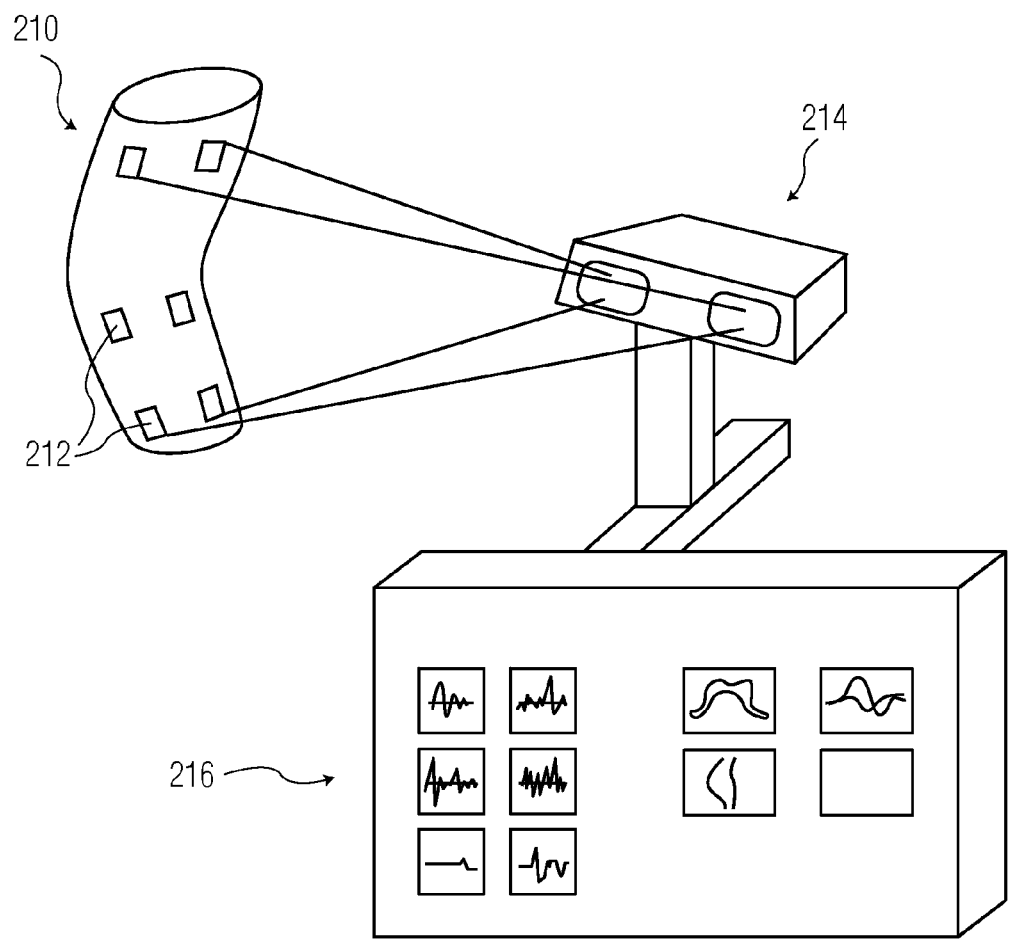
FIG. 5 is a perspective view of a sleeve according to another embodiment of the present invention, shown in conjunction with a camera unit and output device.

Further still, FIG. 5 depicts another embodiment sleeve 210, which may include any of the aforementioned sensor technology and/or provide any of the aforementioned uses. In addition, or alternatively, sleeve 210 includes sensors 212 which are capable of being monitored by tracker 214, which in turn can provide movement data to be outputted via display 216. In one embodiment, sensors 212 are navigation trackers capable of being monitored by camera 214 so as to output movement data to display 216. This embodiment is particularly useful in movement analyses for particular joint, such as a gait analysis for the knee joint. In addition, it is contemplated to incorporate certain of the other sensors discussed above, such as the EMG sensors, to couple the movement analysis with muscle activity. Of course, other embodiments, may employ touch sensors in line with the foregoing.

The present invention improves upon the prior art by making the process patient specific, three-dimensional, and real time through the display of touch related data. This data can be correlated to clinical metrics and pathologies and, as discussed above, can aid in use as a research tool, validation tool, diagnostic tool, and/or kinematic analysis tool.

As noted above, any of the foregoing sleeves can be configured for use in connection with any joint of the body, as well as any other aspect of the body. For instance, it is contemplated that the sleeves can be configured to fit over any portion of the body, including, but not limited to, portions of the arms, legs, and/or trunk. With regard to the latter, the sleeves could be utilized to determine the location and/or severity of pain in the back.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method comprising:
   placing a sleeve over a portion of a body comprising a joint, the sleeve including fabric interwoven with EMG sensors for detecting a location of a touch and a navigation sensor for recording spatial movement, the EMG sensors and the navigation sensor being in communication with a display device;

moving the portion of the body;

tracking the spatial movement of the navigation sensor;

touching a portion of the sleeve corresponding to an area of pain in the portion of the body induced by the movement of the portion of the body; and displaying on the display device information associated with the movement of the navigation sensor and information pinpointing the area of touch corresponding to the area of pain.

2. The method of claim 1, wherein the displaying step includes displaying the area of pain on a visual representation of the portion of the body.

3. The method of claim 1, wherein the touching step is performed with a finger.

4. The method of claim 1, wherein the touching step is performed with a stylus.

5. The method of claim 1, further comprising a step of calibrating the sleeve to the portion of the body.

6. The method of claim 5, wherein the calibrating step includes registering cardinal points by touching the sleeve.

7. The method of claim 6, wherein the portion of the body is a knee joint.

8. The method of claim 7, wherein the cardinal points are selected from the group consisting of the patella, medial and/or lateral epicondyle, tibial tubrical and joint line.

9. The method of claim 1, wherein the area of pain is shown on an avatar corresponding to the portion of the body on a display.

10. The method of claim 1, further comprising a step of determining the pressure of the touch, the greater the pressure corresponding to greater pain.

11. The method of claim 10, further comprising a step of displaying the pressure information.

12. The method of claim 1, wherein the at least one sensor wirelessly communicates with the display device.

13. The method of claim 1, wherein the sensor and the display device are in communication with a computer.

14. The method of claim 1, wherein the touching step includes touching a first portion of the sleeve corresponding to a first area of pain and touching a second portion of the sleeve corresponding to a second area of pain.

15. The method of claim 14, wherein the displaying step includes displaying information pinpointing the first and second areas of pain on the display device.

* * * * *